United States Patent
Hendrickson et al.

(10) Patent No.: US 9,049,880 B2
(45) Date of Patent: Jun. 9, 2015

(54) METHOD FOR HARVESTING COCHINEAL WAX FROM COCHINEAL INSECTS GROWN ON AN ARTIFICIAL MEDIUM

(75) Inventors: Connie M. Hendrickson, Irving, TX (US); Denise Lynn Merkle, Ft. Worth, TX (US)

(73) Assignee: Badderloch Woad, Inc., Irving, TX (US)

( * ) Notice: Subject to any disclaimer, the term of this patent is extended or adjusted under 35 U.S.C. 154(b) by 314 days.

(21) Appl. No.: 13/545,171

(22) Filed: Jul. 10, 2012

(65) Prior Publication Data

US 2013/0015397 A1    Jan. 17, 2013

Related U.S. Application Data

(60) Provisional application No. 61/507,188, filed on Jul. 13, 2011.

(51) Int. Cl.
*A23L 1/275* (2006.01)
*C09B 61/00* (2006.01)

(52) U.S. Cl.
CPC .............. *A23L 1/2751* (2013.01); *C09B 61/00* (2013.01)

(58) Field of Classification Search
CPC ...................................................... C09B 61/00
See application file for complete search history.

(56) References Cited

U.S. PATENT DOCUMENTS

2011/0036295 A1    2/2011    Merkle et al.

FOREIGN PATENT DOCUMENTS

SU              1081188 A  *  3/1984     ............. C09B 61/00

OTHER PUBLICATIONS

English translation of SU 1081188 A, Nersisyan et al., Oct. 15, 2014.*
Chibnall, Albert C. et al., "XLIII. The Constitution of Coccerin."; Biochemical Department, Imperial College of Science and Technology, South Kensington, Received Jan. 8, 1934; 13 pages.
Meinwald, J. et al., "Characterization and Synthesis of Waxes From Homopterous Insects"; J. Chem., Ecol., 1975, vol. 1, No. 2, pp. 269-274.
www.henriettesherbal.com/eclectic/kings/coccus.html; "Henriette's Herbal Homepage"; Apr. 21, 2011; 4 pages.
Online Encyclopedia; http://encyclopedia.jrank.org/NUM_ORC/OILS; OILS (adopted from the Fr. oile, mod. huile, Lat. oleum, olive oil); Apr. 21, 2011; 6 pages.

* cited by examiner

*Primary Examiner* — Rosanne Kosson
(74) *Attorney, Agent, or Firm* — John A. Fortkort; Fortkort & Houston P.C.

(57) ABSTRACT

A method for obtaining cochineal wax is provided which comprises (a) harvesting cochineal insects from an artificial medium inoculated with the insects; (b) extracting cochineal wax from the insects with a liquid medium; and (c) isolating cochineal wax from the liquid medium.

21 Claims, 1 Drawing Sheet

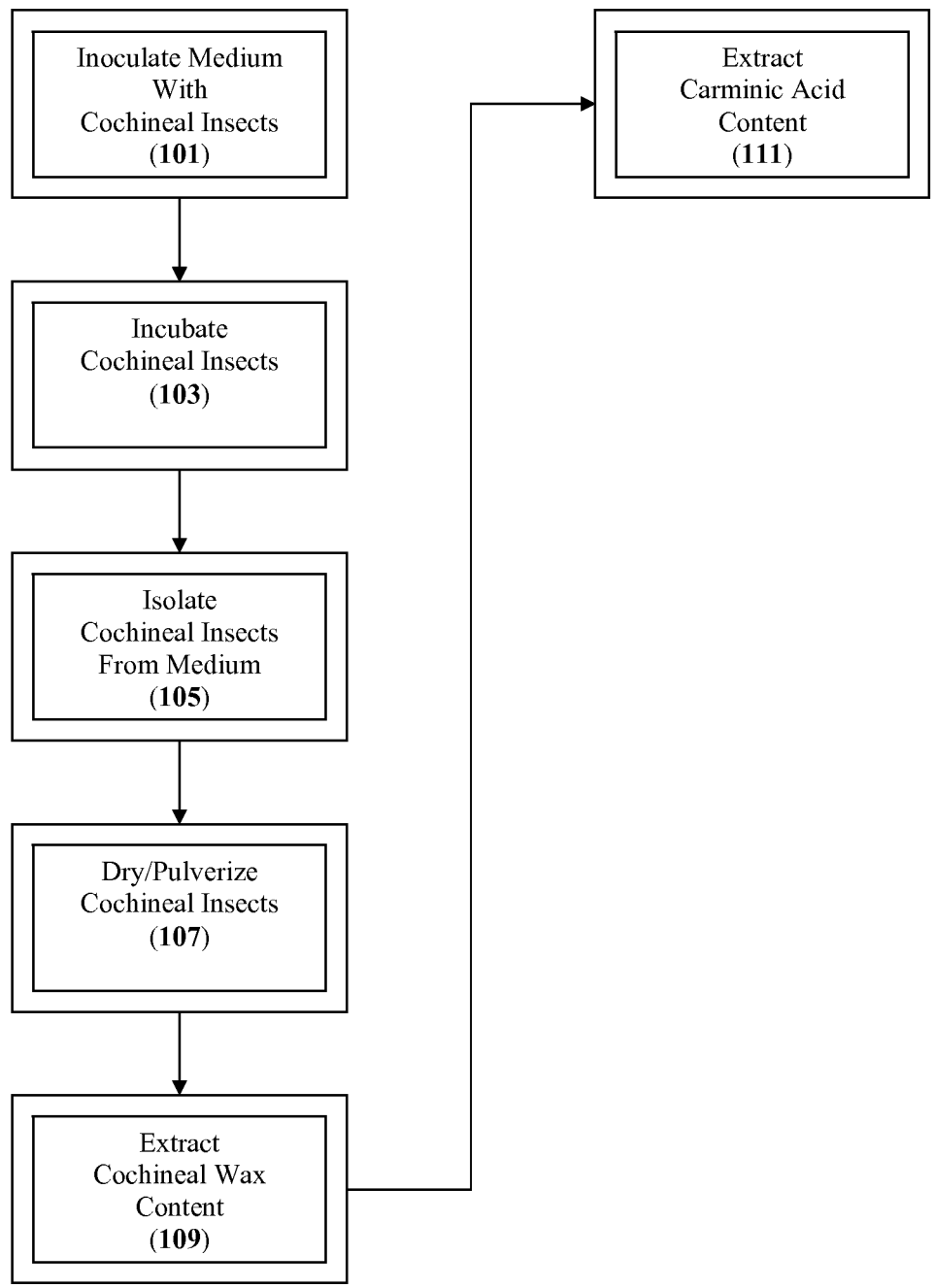

METHOD FOR HARVESTING COCHINEAL WAX FROM COCHINEAL INSECTS GROWN ON AN ARTIFICIAL MEDIUM

CROSS REFERENCE TO RELATED APPLICATION

This application claims the benefit of U.S. Provisional Application No. 61/507,188, filed Jul. 13, 2011, having the same title, and having the same inventors, and which is incorporated herein by reference in its entirety.

FIELD OF THE DISCLOSURE

The present disclosure relates generally to naturally occurring waxes, and more particularly to systems and methods for harvesting wax from cochineal insects which have been incubated on an artificial medium.

BACKGROUND OF THE DISCLOSURE

Carmine (also called cochineal) is a deep red, naturally occurring dye which has been used for thousands of years by populations in Central and North America. Despite the difficulty of producing carmine, the colorant is still in widespread demand. Carmine is an FDA approved additive, and is used to enhance the appearance of food, confections, pharmaceuticals and cosmetics. In addition, its staining properties make it an excellent contrasting agent for microbiological studies and cellular research. Carminic acid (see STRUCTURE I below), which is the dominant chromophoric ingredient in carmine, is naturally produced during the life cycle of female insects of the genus *Dactylopius*, such as those of the species *Dactylopius coccus* (referred to herein as cochineal insects).

STRUCTURE I

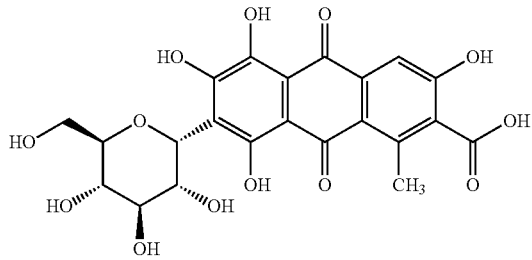

Cochineal insects occur naturally as parasites on cacti of the genus *Opuntia*, with *Opuntia ficus-indica* being the most suitable host. Historically, cultivation of cochineal insects for large scale harvest was initiated through careful inoculation of cacti with infected cactus pads or with pathogen-free females. Typically, in this approach, the insects are introduced to the host via baskets known as Zapotec nests. After inoculation, the cochineal insects must be protected from predators and from harmful weather conditions during their 3 month growth cycle.

Carmine is then laboriously extracted from the tiny (about 0.2 inch or 0.5 cm in length) female cochineal insects after the pads of the inoculated cacti are gathered. Approximately 155,000 insects are required to yield a single kg of carminic acid. The harvesting process is a labor and time intensive endeavor, and typically involves removing the cochineal insects by hand from the infected cactus pads.

More recently, it has been discovered that cochineal insects can be cultivated on an artificial medium. The details of this process may be found in commonly assigned U.S. 2011/0036295 (Merkle et al.), entitled "MEANS TO CULTURE COCHINEAL INSECTS IN AN ARTIFICIAL MEDIUM", which was filed on Feb. 26, 2010, and which is incorporated herein by reference in its entirety. This approach has opened the door for widespread laboratory cultivation of cochineal insects.

SUMMARY OF THE DISCLOSURE

In one aspect, a method is provided for obtaining cochineal wax. The method comprises (a) harvesting cochineal insects from an artificial medium inoculated with the insects; (b) extracting cochineal wax from the insects with a liquid medium; and (c) isolating cochineal wax from the liquid medium.

In another aspect, a method for obtaining cochineal wax is provided. The method comprises (a) inoculating an artificial medium with cochineal insects; and (b) extracting cochineal wax from the insects with a liquid medium.

In a further aspect, a method is provided for obtaining cochineal wax. The method comprises (a) inoculating an artificial medium with cochineal insects; (b) pulverizing the inoculated medium; and (c) extracting cochineal wax from the pulverized medium.

In still another aspect, a composition of matter is provided which comprises an artificial medium inoculated with cochineal insects.

BRIEF DESCRIPTION OF THE DRAWINGS

FIG. 1 is flowchart for a process of recovering cochineal wax and carminic acid from cochineal insects in accordance with an embodiment of the methodologies disclosed herein.

DETAILED DESCRIPTION

U.S. 2011/0036295 (Merkle et al.), which has been incorporated by reference herein, discloses methods for cultivating cochineal insects, or other species selected from the genus *Dactylopius*, in a suitable artificial medium. Such an artificial medium may be fabricated, for example, from a curable or hardenable medium which contains a cactus additive such as, for example, cactus pulp, cactus nectar, or cactus powder. Preferably, the cactus additive is obtained from the genus *Opuntia*. The curable or hardenable medium may itself be derived from a carbohydrate and a suitable polysaccharide stock. Preferably, the carbohydrate is a monosaccharide, and even more preferably, the carbohydrate is glucose. Corn syrup is an especially preferred source of the carbohydrate. The polysaccharide stock may comprise a material such as Agar, agarose, agaropectin, carrageenan, or other suitable polysaccharides. The curable or hardenable medium may itself be derived from a carbohydrate and/or a suitable polysaccharide stock. Preferably, the carbohydrate is a monosaccharide, and even more preferably, the carbohydrate is glucose. Corn syrup is an especially preferred source of the carbohydrate in those embodiments which utilize one, though it is important to note that various embodiments are possible which do not utilize corn syrup or any other sugars. The polysaccharide stock may comprise a material such as Agar, agarose, agaropectin, carrageenan, or other suitable polysaccharides.

As noted above, the methodologies disclosed in U.S. 2011/0036295 (Merkle et al.) have opened the door for widespread laboratory cultivation of cochineal insects. However, these methodologies have also been found to have further benefits as well. In particular, with suitable modification, these methodologies provide a convenient means by which useful products in addition to carmine may be recovered from cultivated cochineal insects.

The presence of cochineal insects on its native host, prickly pear (*Opuntia*), is typically indicated by a white, cottony substance. This substance, which has the appearance of mold or silk, is coccerin (also called cochineal wax), a waxy mixture secreted by the insects. Chemically, cochineal wax is known to contain predominantly cocceric acid (coccerylic acid, $C_{31}H_{62}O_3$, mp 92-93° C.) and cocceryl alcohol ($C_{30}H_{62}O_2$, mp 101-104° C. or $C_{30}H_{60}(OH)_2$). Cochineal wax provides protection for the insects and their colonies. Moreover, developing insects use strands of the material to catch the wind and sail to new locations to form new colonies.

While the chemical composition of cochineal wax has been known for some time, it has heretofore existed as little more than an academic curiosity. Traditional cochineal insect farming, which is an established practice going back many hundreds of years, has focused on the collection of female insects, since they are the primary source of carmine Much of the cochineal wax content produced by cochineal insects is not collected. This includes cochineal wax present in secretions on the infested host plant and in cocoons produced by the insects, as well as cochineal wax present in the bodies of nymphs and male insects.

Although cochineal wax is also present in the bodies of female insects and is incidentally collected as a result in conventional cochineal insect farming, this content is typically discarded during subsequent processing. Thus, defatting solvents, such as methylene chloride, are typically used to clear the wax from cochineal preparations prior to processing and conversion of carminic acid to carmine Hence, cochineal wax has heretofore been treated as an undesirable byproduct in the production of carmine Undoubtedly, this is due in part to the relatively small amounts of cochineal wax afforded by traditional cochineal insect harvesting.

However, it has now been found that, with suitable modification, the methodologies described in U.S. 2011/0036295 (Merkle et al.) are capable of yielding much larger amounts of cochineal wax than would be afforded by traditional cochineal farming techniques. Without wishing to be bound by theory, this result is believed to be due to the fact that all of the sources of cochineal wax associated with cochineal insects (including both male and female insects and nymphs, cocoons, and secretions) may be readily subjected to the extraction process used in this reference to recover carminic acid from the insects, thus resulting in significantly greater portions of cochineal wax in the extract. Consequently, with the addition to this process of a suitable wax extraction or wax isolation technique, it is possible to economically recover cochineal wax as a valuable byproduct of this process.

FIG. 1 illustrates a first particular, non-limiting embodiment of a method for harvesting cochineal wax in accordance with the teachings herein. The particular embodiment illustrated is implemented as part of a process for growing cochineal insects on an artificial medium for extraction of carminic acid therefrom, it being understood that the systems and methodologies described herein are also applicable to harvesting wax from cochineal insects grown in the wild, either in conjunction with, or apart from, a carminic acid extraction process.

With reference to FIG. 1, a suitable medium is inoculated 101 with cochineal insects. The insects are then incubated 103, and are subsequently isolated 105 from the medium when they have attained a suitable age. The isolated insects are then dried and pulverized 107 (this step may be omitted in some embodiments), after which cochineal wax 109, and then carminic acid 111, are extracted from the insects. Suitable techniques for wax extraction in the context of this embodiment are described below.

The importance of naturally-derived waxes in coatings, food, lighting, fuels, art supplies, polishes, and other such products cannot be overstated. Given the similarities of the coccerin components to waxes in widespread/ubiquitous use, and its higher melting points (mp) than some animal and vegetable waxes and fats, the efficient and effective production of purified coccerin and its components has the potential to significantly augment or even replace waxes currently in use.

Cocceric acid, the hydroxylated acid of the form $C_nH_{2n}O_3$, is in the same series as lanolin or lanopalmitic acid ($C_{16}H_{32}O_3$, mp 87-88° C.), the useful and valuable wax which is isolated from sheep's wool. Cocceryl alcohol (cocceryl coccerate, $C_{30}H_{62}O_2$, mp 101-104° C.) is an alcohol of the glycolic series $C_nH2_{n+2}O_2$, and is a branched ester (mp 103.5-103.8° C.) present in carnauba wax, a valuable hard wax isolated from the Brazilian palm, *Copernicia prunifera*. Myrisyl alcohol, a component of beeswax, is also present in small amounts in cochineal wax. Beeswax is used for polishing, candles, skin care products, and foodstuffs. It will thus be appreciated that Coccerin and its components have the potential to be valuable to the pharmaceutical and food industries, in skin care products, as coatings and additives for coatings on paper and other substrates, for polishes and surface waxes, and as art supplies (such as, for example, Chinese wax (insect wax, ceryl cerotate, mp 82.5° C., derived from *Coccus ceriferus*)).

Cochineal wax may be readily extracted from culture-grown insects. In a preferred embodiment of the extraction process, the growth medium, either fresh or dried, is scraped of all cochineal material, including wax, cocoons, nymphs, pregnant females, and the like. This collected and combined material is then be crushed and boiled in hot distilled water. This dark red preparation is preferably cooled below 60° C. so that the wax, with a melting point of ~100-102° C., solidifies and floats to the top, allowing for easy removal. The hot water extract may then be concentrated by evaporation, and the resulting flat, dark red crystals of carminic acid may be converted to carmine by published methods. Advantageously, this procedure reduces or eliminates the need for organic solvents.

While the foregoing embodiment is the preferred methodology for extracting cochineal wax from culture-grown insects, other methodologies may be utilized as well. Preferably, these methodologies involve extracting the cochineal wax with a liquid medium which is heated to a first temperature $T_1$, wherein $T_1 > Tmp_{wax}$, and wherein $Tmp_{wax}$, is the melting point of cochineal wax. The cochineal wax is then preferably extracted from the liquid medium by cooling the liquid medium to a second temperature $T_2$, wherein $T_2 < Tmp_{wax}$. Preferably, $T_1 > 102°$ C. and more preferably, $T_1 > 110°$ C. Preferably, $T_2 < 60°$ C. and more preferably, $T_2 < 40°$ C.

Of course, it will be appreciated that various modifications may be made to the foregoing process. For example, in some embodiments, the inoculated growth medium may be crushed or pulverized to form a powder or other particulate mass from which cochineal wax and carminic acid may be readily extracted.

It will also be appreciated that the systems and methods described herein for obtaining cochineal wax are not limited to use with cochineal insects grown on an artificial medium, though such a use is preferred. Hence, for example, these systems and methodologies may be applied to the production of cochineal wax from insects grown in the wild (e.g., on prickly pear farms).

It will further be appreciated that the cochineal insects and the medium they are grown on (which may be natural or artificial) may or may not be dried prior to pulverization or wax extraction, assuming that these steps are utilized in the first place. Moreover, while wax extraction with hot $H_2O$ is preferred, one skilled in the art will appreciate that various solvent systems may be utilized in place of, or in addition to, hot $H_2O$.

Finally, it will be appreciated that various additional steps may be performed in the processes described herein. By way of example, the recovered wax may be subjected to various purification processes including, without limitation, various filtration or distillation techniques.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A method for obtaining cochineal wax, comprising:
    providing an artificial medium inoculated with cochineal insects;
    culturing the cochineal insects on the inoculated medium;
    extracting cochineal wax from the cochineal insects with a liquid medium; and
    isolating the cochineal wax from the liquid medium.

2. The method of claim 1, wherein extracting cochineal wax from the cochineal insects with a liquid medium involves heating the liquid medium to a first temperature $T_1$, wherein $T_1 > Tmp_{wax}$, and wherein $Tmp_{wax}$ is the melting point of cochineal wax.

3. The method of claim 2, wherein isolating the cochineal wax from the liquid medium involves cooling the liquid medium to a second temperature $T_2$, wherein $T_2 < Tmp_{wax}$.

4. The method of claim 3, wherein $T_1 > 102°$ C.

5. The method of claim 3, wherein $T_1 > 110°$ C.

6. The method of claim 3, wherein $T_2 < 60°$ C.

7. The method of claim 1, wherein the liquid medium is an aqueous medium.

8. The method of claim 6, wherein the liquid medium is an aqueous medium, wherein the wax floats to the top of the liquid medium when the liquid medium is cooled to the second temperature, and wherein isolating cochineal wax from the liquid medium further involves collecting the wax from the surface of the liquid medium.

9. The method of claim 1, further comprising harvesting the cochineal insects from the inoculated medium;
    wherein the cochineal insects are pulverized after they are harvested and before the cochineal wax is extracted.

10. The method of claim 1, further comprising:
    harvesting the cochineal insects from the artificial medium prior to extracting cochineal wax from the cochineal insects;
    wherein harvesting the cochineal insects includes removing both male and female insects from the artificial medium.

11. The method of claim 1, further comprising:
    harvesting the cochineal insects from the artificial medium prior to extracting cochineal wax from the cochineal insects;
    wherein harvesting the cochineal insects includes removing cochineal wax from the artificial medium.

12. The method of claim 1, further comprising:
    harvesting the cochineal insects from the artificial medium prior to extracting cochineal wax from the cochineal insects;
    wherein harvesting the cochineal insects includes harvesting the cocoons of cochineal insects from the artificial medium.

13. The method of claim 1, further comprising:
    harvesting the cochineal insects from the artificial medium prior to extracting cochineal wax from the cochineal insects;
    wherein harvesting cochineal insects from an artificial medium includes harvesting cochineal nymphs from the artificial medium.

14. The method of claim 1, wherein the artificial medium comprises a plant additive and a polysaccharide.

15. The method of claim 14, wherein the plant additive is a cactus additive.

16. The method of claim 15, wherein the cactus additive is derived from the genus *Opuntia*.

17. The method of claim 1, further comprising:
    drying the cochineal insects prior to harvesting them;
    wherein the cochineal insects are dried to about 20% to about 40% of their original body weight.

18. The method of claim 1, further comprising harvesting the cochineal insects from the inoculated medium, wherein harvesting cochineal insects from the inoculated medium includes:
    drying the inoculated medium; and
    pulverizing the dried medium to generate a particulate mass.

19. The method of claim 18, wherein the particulate mass contains cochineal wax content, and wherein the cochineal wax content is chemically extracted from the particulate mass.

20. The method of claim 19, wherein the particulate mass contains cochineal dye content, and wherein the cochineal dye content is also chemically extracted from the particulate mass.

21. The method of claim 20, wherein a mixture of the cochineal dye content and the cochineal wax content is chemically extracted from the particulate mass, and further comprising isolating the cochineal wax content from the mixture.

* * * * *